(12) United States Patent
Fenc

(10) Patent No.: US 7,112,064 B1
(45) Date of Patent: Sep. 26, 2006

(54) DENTURE

(76) Inventor: Jerry Fenc, 413 Guildwood Pky. West Hill, Ontario (CA) M1E 1R3

(*) Notice: Subject to any disclaimer, the term of this patent is extended or adjusted under 35 U.S.C. 154(b) by 0 days.

(21) Appl. No.: 11/103,106

(22) Filed: Apr. 11, 2005

(51) Int. Cl.
*A61C 13/24* (2006.01)

(52) U.S. Cl. .................................. 433/185; 433/188
(58) Field of Classification Search ............ 433/168.1, 433/184, 185, 186, 187, 188
See application file for complete search history.

(56) References Cited

U.S. PATENT DOCUMENTS

| | | | |
|---|---|---|---|
| 287,199 A | 10/1883 | Van Vleck | |
| 323,306 A | 7/1885 | Evans | |
| 909,038 A | 1/1909 | Telle | |
| 1,612,605 A | 12/1926 | Buenaventura | |
| 2,392,513 A | 1/1946 | Town | |
| 2,867,903 A * | 1/1959 | Hedges | 433/187 |
| 3,083,459 A | 4/1963 | McMurry et al. | |
| 3,657,815 A | 4/1972 | Powell | |
| 3,722,096 A * | 3/1973 | Kopfer et al. | 433/184 |
| 3,886,659 A * | 6/1975 | Reifke | 433/188 |
| 4,202,098 A | 5/1980 | Russo | |
| 4,439,153 A | 3/1984 | Kawahara et al. | |
| 4,634,381 A * | 1/1987 | Kusano et al. | 433/172 |
| 4,824,373 A | 4/1989 | Okada et al. | |
| 6,705,866 B1 | 3/2004 | Okamoto | |
| 2004/0029076 A1 | 2/2004 | Nowack | |

* cited by examiner

*Primary Examiner*—Cary E. O'Connor
(74) *Attorney, Agent, or Firm*—Blackwell Sanders Peper Martin LLP

(57) ABSTRACT

A denture has a body with a plurality of concavities in a first surface of the body—the first surface, in use, abutting soft tissue of the mouth. A plurality of through holes extend from the first surface to an opposite, second, surface.

11 Claims, 9 Drawing Sheets

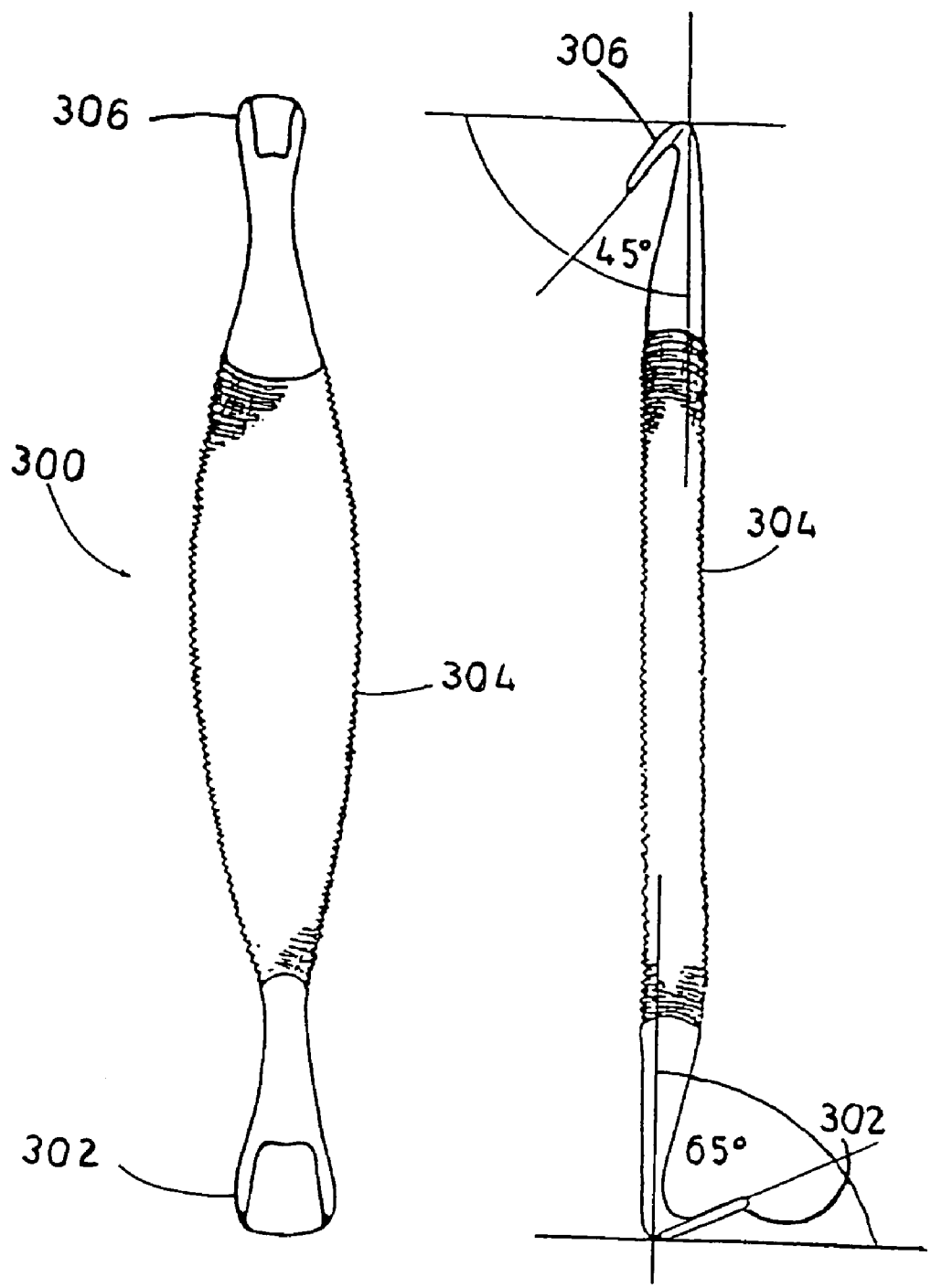
FIG. 10 A  FIG. 10 B

DENTURE

BACKGROUND OF INVENTION

This invention relates to dentures.

An individual who has lost a number of, or all of, his teeth may wear a denture. If any remaining teeth are insufficient to moor the denture, a dental adhesive is typically used to secure the denture in place. However, a denture secured by an adhesive may fail to remain in place, particularly when the wearer is masticating.

Therefore, there remains a need for a denture that can more securely be held in place in the mouth.

SUMMARY OF INVENTION

A denture has a body with a plurality of concavities in a first surface of the body—the first surface, in use, abutting soft tissue of the mouth. A plurality of through holes extend from the first surface to an opposite, second, surface.

Accordingly, the present invention provides a denture comprising: a body having a plurality of concavities in a first surface of said body, said first surface, in use, abutting soft tissue of a mouth and a plurality of through holes extending from said first surface to an opposite, second, surface.

Other features and advantages will become apparent from a review of the drawings in conjunction with the accompanying description.

BRIEF DESCRIPTION OF THE DRAWINGS

In the figures which illustrate example embodiments of the invention,

FIG. 10A is a front view of a tool for use with the dentures of FIGS. 1 to 5A, 7, and 8, and FIG. 10B is a side view of the tool of FIG. 1A.

DETAILED DESCRIPTION

Figure 1:
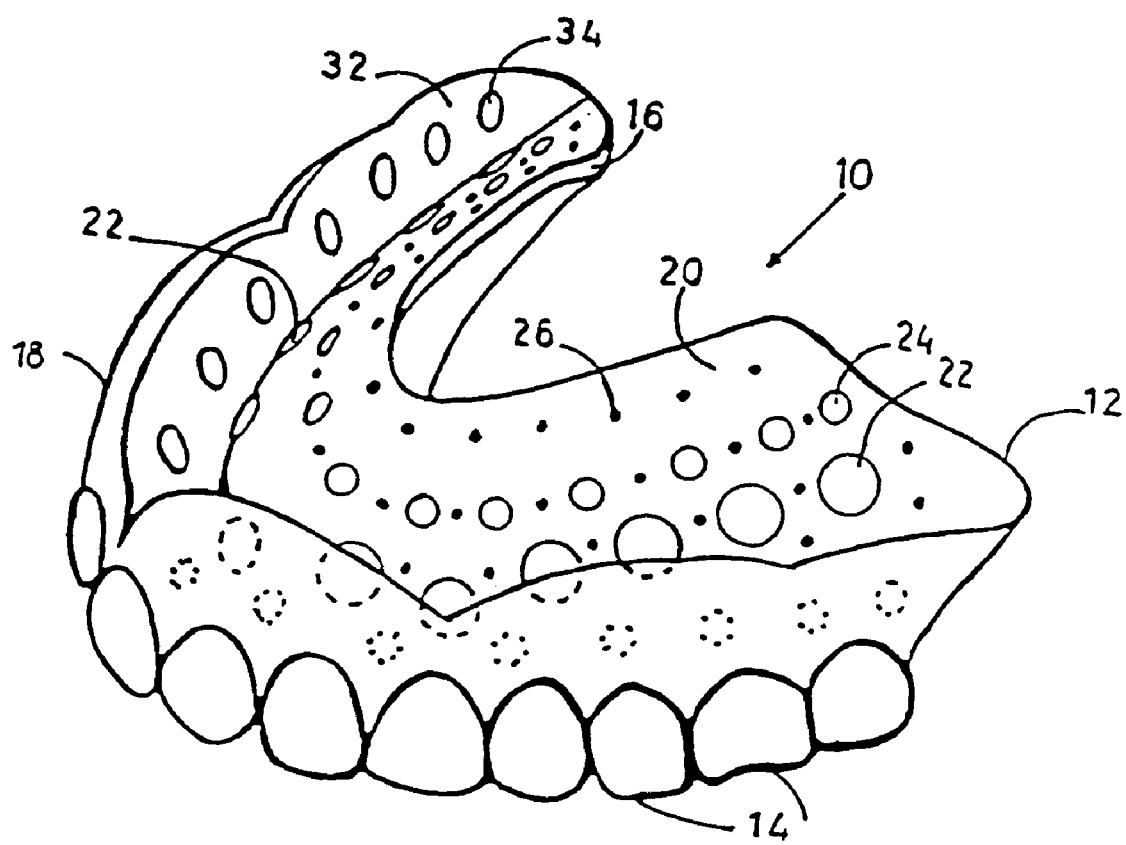
FIG. 1A is a top front perspective view of a maxillary denture made in accordance with this invention.
FIG. 1B is a top rear perspective view of the denture of FIG. 1.
Figure 1:
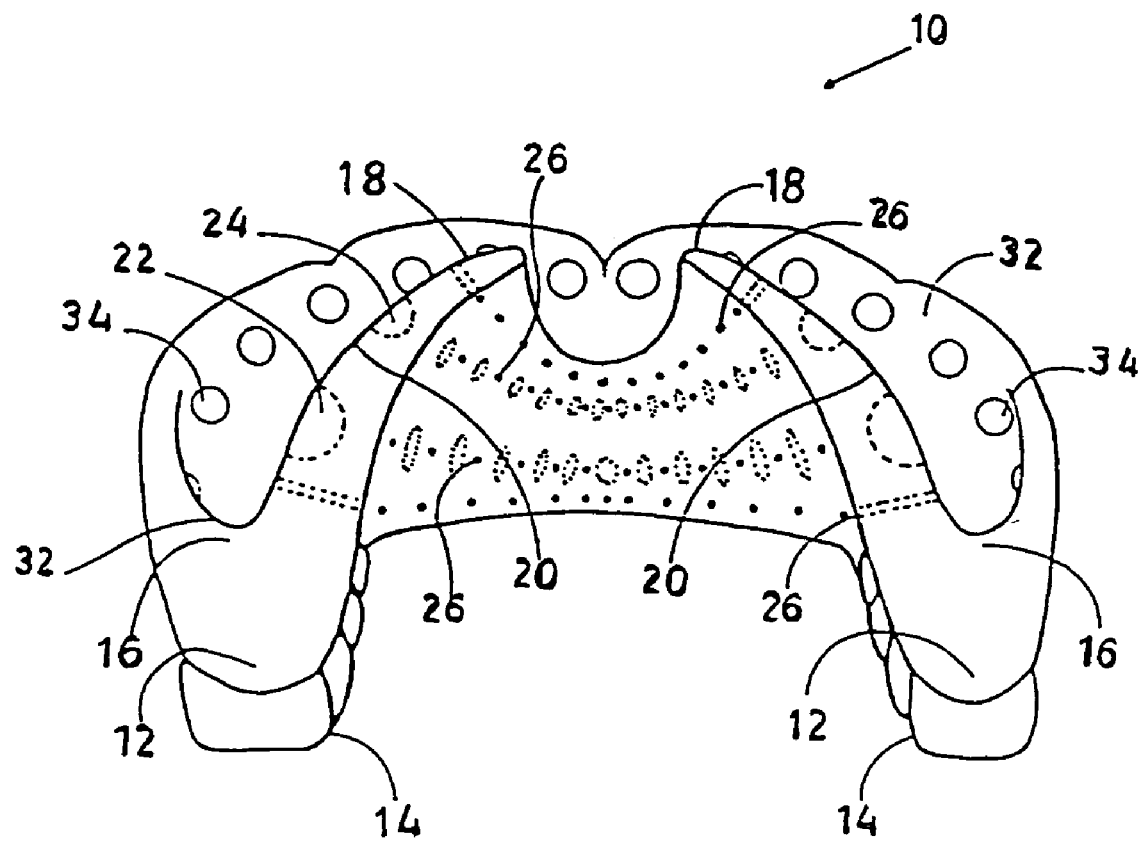
Figure 3:
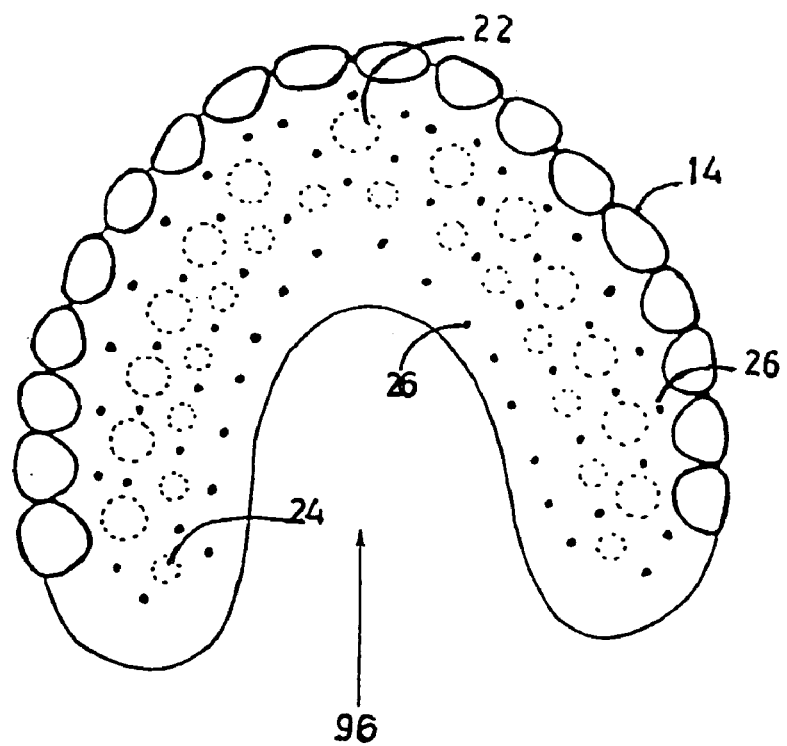
FIG. 3 is a bottom view of the denture of FIG. 1.

Turning to FIGS. 1A and 1B, a maxillary denture 10 has a body 12 supporting teeth 14. The body has a base section 16 and an upstanding section 18. An upper surface 20 of the base section 16 of the body 12 has a plurality of larger concavities 22 and smaller concavities 24. A plurality of through holes 26 extend from the upper surface 20 to the opposite, lower, surface 30 (FIG. 3) of the base section 16. An inner surface 32 of the upstanding section 18 has a second plurality of smaller concavities 34.

The base section 16 of the denture 10 may have a thickness of about 9 mm (compared with a usual thickness of about 5 mm for a typical denture) and taper toward its rear edge. The upstanding section 18 may taper in thickness toward its top edge. The concavities 22, 24, 32 may have a part spherical shape. The larger concavities 22 may have a diameter at surface 20 of about 4 mm and a depth of about 4 mm. The smaller concavities 24 (which are closer to the rear edge of the denture) may have a diameter at surface 20 of about 3 mm and a depth of about 3 mm. The smaller concavities 32 may be similarly dimensioned.

Figure 2:
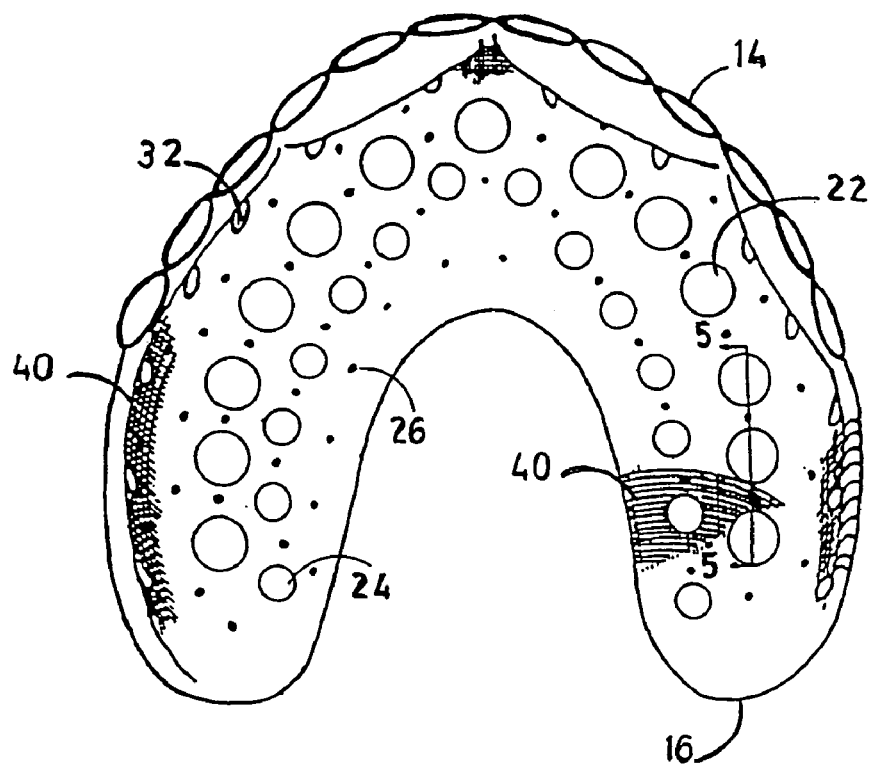
FIG. 2 is a top view of the denture of FIG. 1.
Figure 4:
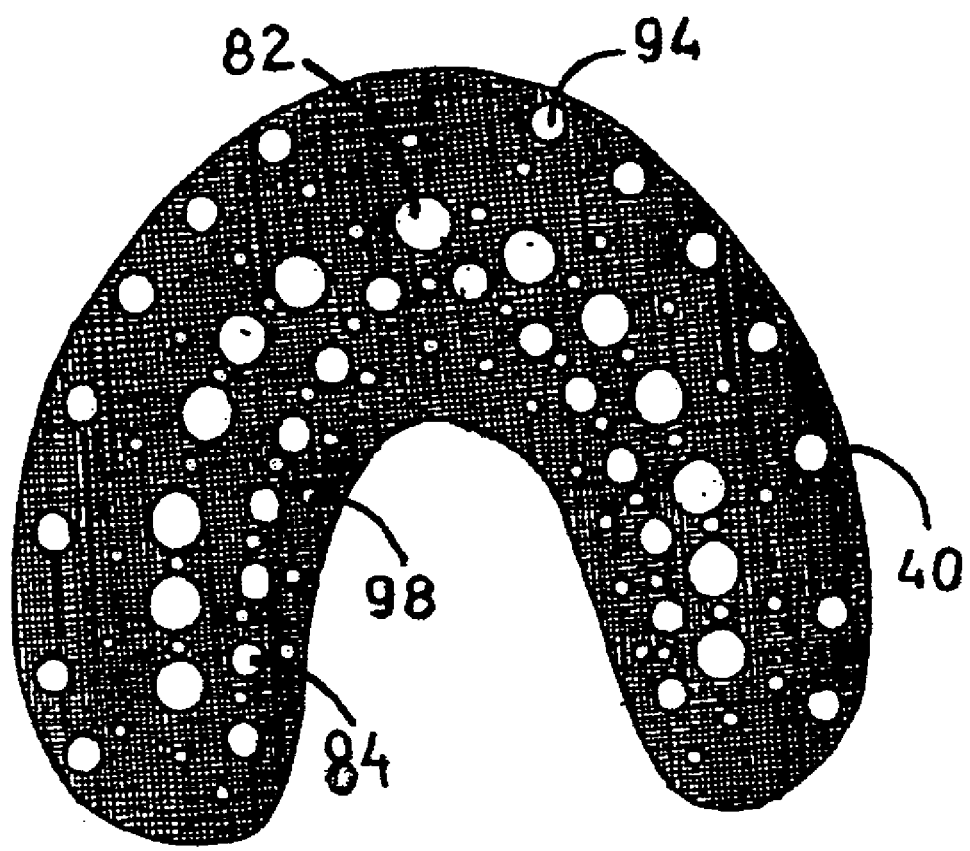
FIG. 4 is a view of a membrane used in the denture of FIG. 1.

With reference to FIG. 2, a porous membrane 40 is adhered to the top surface 20 of base section 16 of the denture. The porous membrane does not extend across the through holes 26 nor the concavities 22, 24, 34. The membrane 40 is detailed in FIG. 4. From this it will be apparent that the membrane is provided with openings 82, 84, 94 which, when the membrane is adhered to the denture, register with concavities 22, 24, 34 (FIG. 1A). The membrane is also provided with circular markings 98 which are used as targets for forming through holes 26, as will shortly be explained.

The porous membrane 40 may comprise a microporous material, such as GORETEX™.

Holes 82, 84, 94, 98 may be stamped out of a membrane sheet 40. Denture 10 may be fabricated by molding a resin composition (such as PROFLEX NFC™ resin) to form base 16 and upstanding section 18. After the resin is cured, the membrane 40 may be bonded to the upper surface 20 of denture 10. Concavities 22, 24, 34 and through holes 26 may then be drilled into the denture, with the holes 82, 84, 94 in membrane 40 acting as a template to show the location for the concavities and the holes 98 acting as a template to properly locate a drill bit to drill through holes 26.

Figure 6:
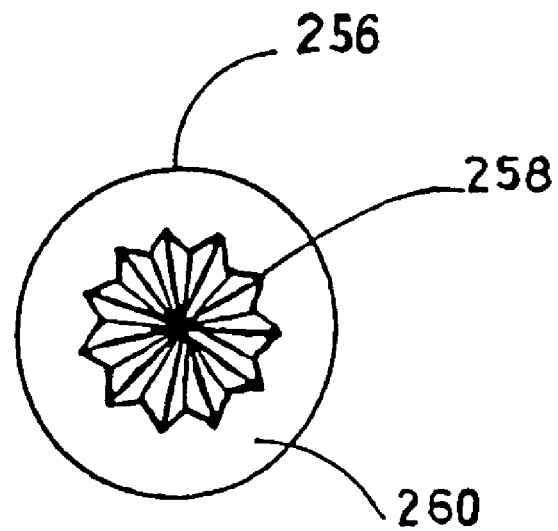
FIG. 6A is a side view of a drill bit used in fabricating a denture made in accordance with this invention.
FIG. 6B is a top view of the drill bit of FIG. 6A.
Figure 6:
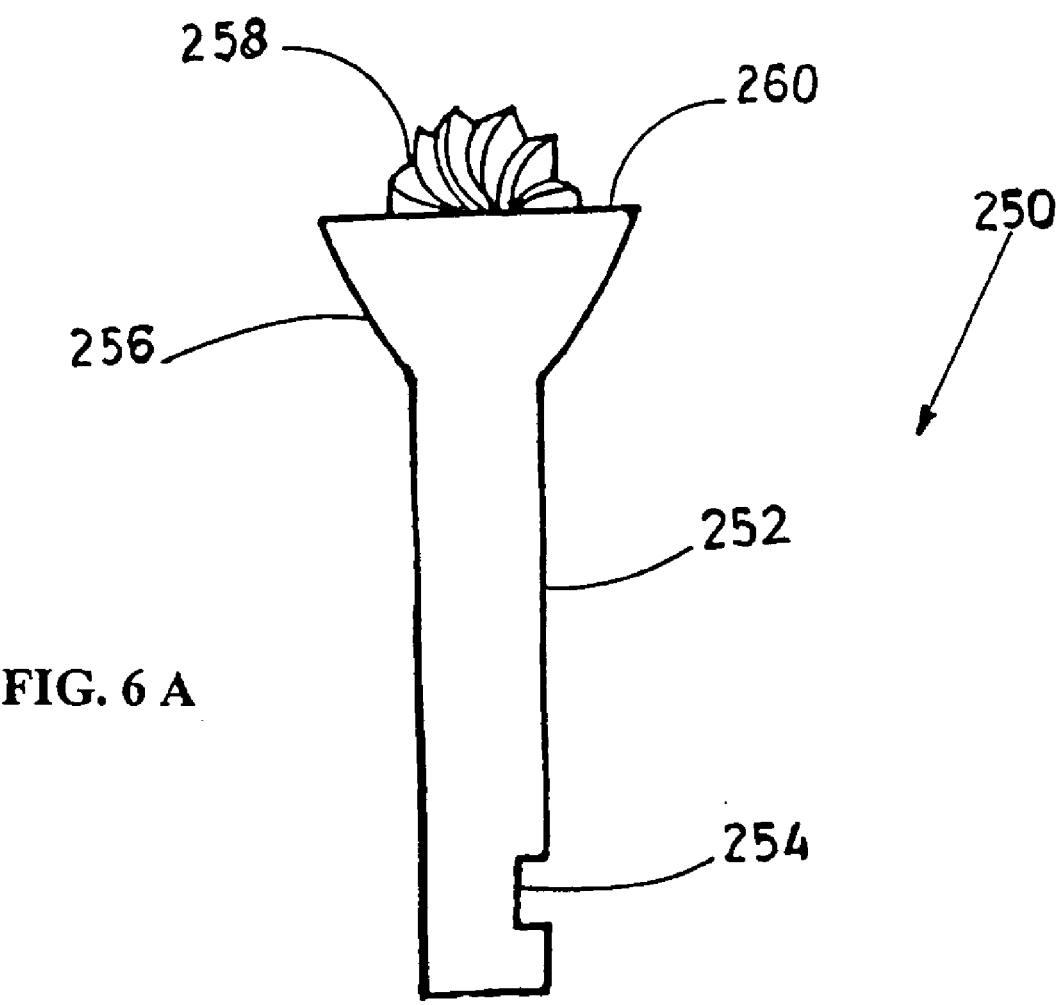

Through holes 26 may be drilled with a standard drill bit. Concavities 22, 24, 34 may be drilled with special purpose bits configured as illustrated in FIGS. 6A and 6B. Referencing these figures, a drill bit 250 has a shank 252 with a notch 254 which may be used to lock the bit into a drill so that the bit will not slip axially during drilling. The head 256 of the bit has a cutting end 258 and a shoulder 260. In use, when drilling concavities with a drill bit 250, the shoulder 260 of the bit will limit the depth of the concavity. Thus, by drilling until the shoulder impacts the denture, each concavity can be drilled to a set depth. A different sized bit will be used for the larger concavities 22 than that which is used to drill the smaller concavities 24, 32 with the height and diameter of the bit cutting end 258 setting the depth and diameter of the concavity. To avoid damage to the membrane 40 when the shoulder 260 of the bit impacts the denture, the membrane may be provided with a disposable cling-on, or adhesively adhered, plastic covering. This covering is added to the membrane before the holes 82, 94 are punched in the membrane so that such holes are also punched in the plastic covering. After drilling of all of the concavities, the plastic covering may then be removed. Alternatively, the concavities may be drilled before the membrane 40 is adhered to the denture using a disposable template which matches the pattern of holes 82, 94 in the membrane.

Figure 5:
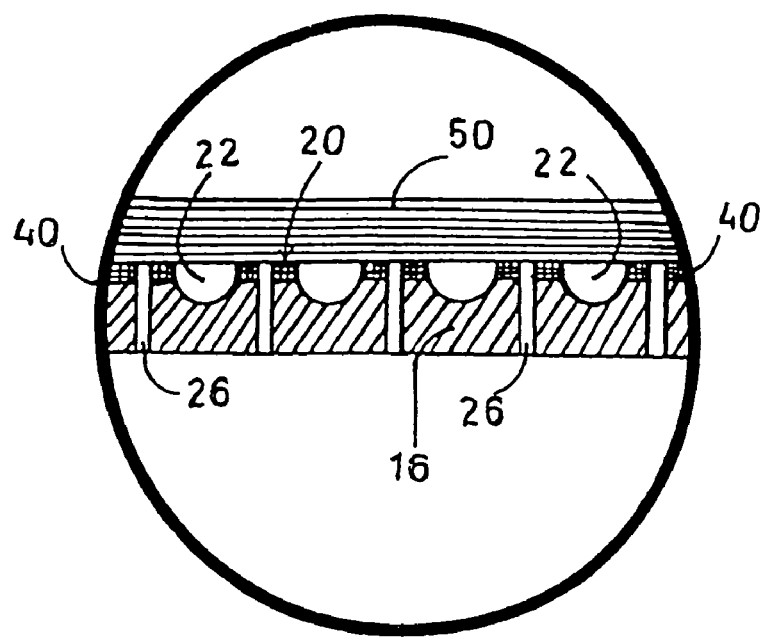
FIG. 5 is a cross-sectional fragmentary view along the lines 5—5 of FIG. 2, showing the denture in use.
Figure 5A:
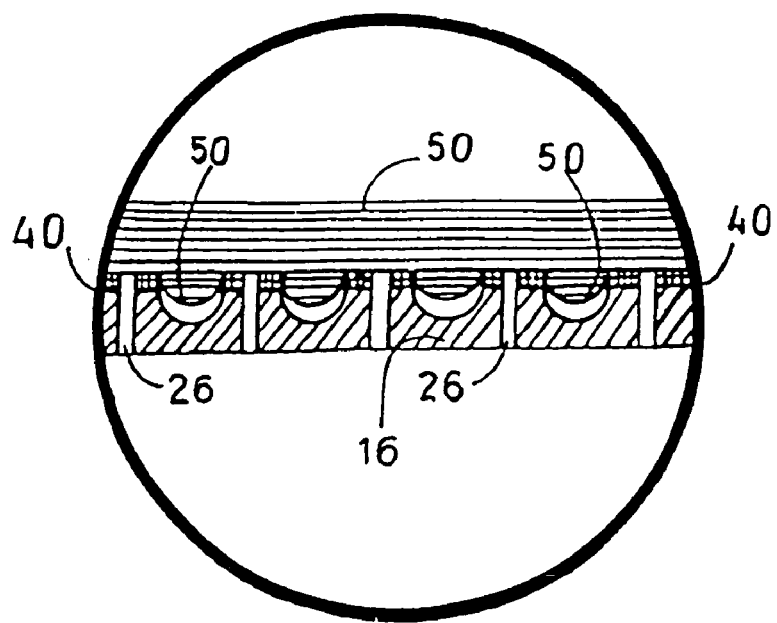
FIG. 5A is another cross-sectional fragmentary showing the denture in use.

With reference to FIGS. 1A and 5, in use, the maxillary denture 10 is placed in the mouth so that the upper surface 20 of base 16 of the denture abuts the soft tissue 50 at the roof of the mouth of the user and the inner surface 32 of the upstanding portion 18 of the denture abuts gum tissue in the mouth of the user. With reference to FIG. 5A, the user may then bite down on the denture, as a result of, for example, masticating. When this occurs, the soft tissue 50 at the roof of the mouth is pressed into the concavities 22 and 24 in the denture (and, to a lesser extent, gum tissue is pressed into concavities 34 in the denture). As this tissue enters the concavities, the air in the concavities is pressurised and pushed out of the concavities through porous membrane 40 which is interposed between the concavities and the through holes 26. The air pushed through the membrane 40 then enters through holes 26 and vents into the mouth.

When the user releases his bite, the weight of the denture 10 will urge tissue 50 to withdraw from concavities 22 and 24 (and will urge gum tissue to withdraw from concavities 34). However, this urging will be resisted by the resulting partial vacuum in the concavities. This partial vacuum will create a pressure differential between air in the through holes 26 and concavities 22 (and 24 and 34), with the higher pressure air now being in the through holes. Despite this, with an appropriate choice of material for membrane 40 little air will migrate through the material of membrane 40. This is for the reason that the pressure differential resulting from release of a bite will normally be much smaller than the pressure differential created by biting down. Indeed, the forces from masticating can be quite extreme, and far greater than the forces from the influence of gravity on the denture. Thus, the concavities act as suction cups which retain the denture in place.

Figure 7:
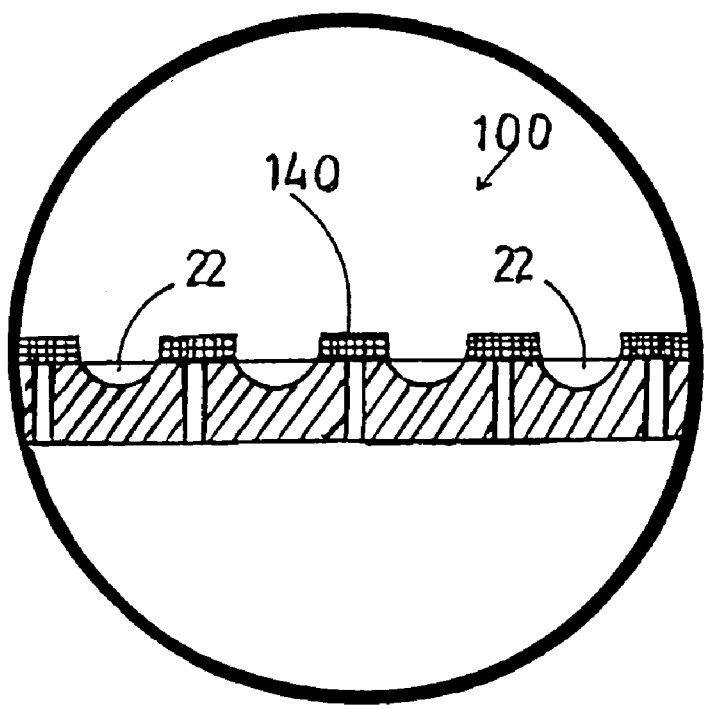
FIG. 7 is a cross-sectional fragmentary view of a denture made in accordance with another embodiment of this invention.

The central area 96 (FIG. 3) of the denture 10 is cut away to allow saliva generated by tissue 50 to reach food in the mouth. Additionally, through holes 26 provide a passage for saliva generated by tissue 50. Optionally, where sufficient saliva is provided by the cut away area 96 of the denture, the through holes may be capped with the material of membrane 40, as illustrated by membrane 140 of denture 100 in FIG. 7. In such instance, as a further option, rather than providing through holes 26 spaced from the concavities 22, 24, these holes could be provided within the concavities and small patches of the material of membrane 40 bonded to the denture within the concavities to cover the through holes.

Figure 8:
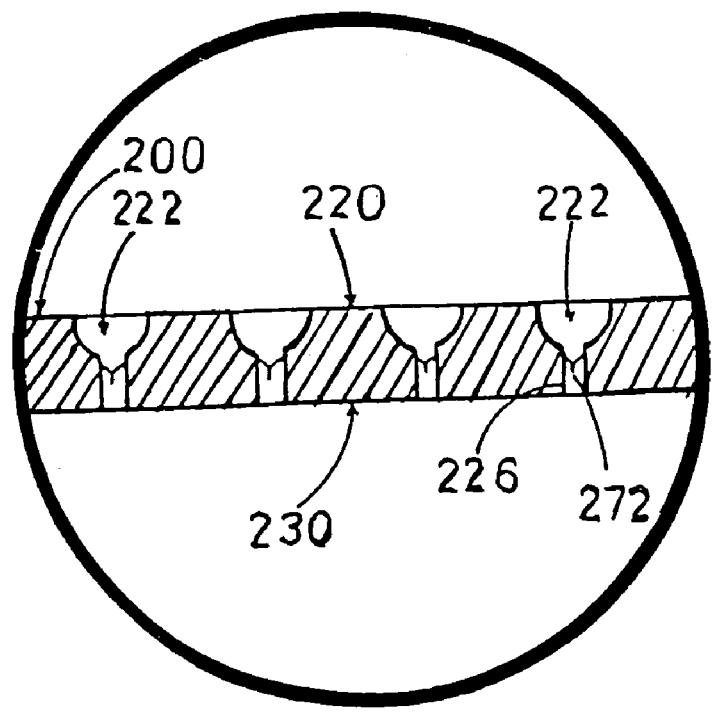
FIG. 8 is a cross-sectional fragmentary view of a denture made in accordance with another embodiment of this invention.

With reference to FIG. 8, in another embodiment, a denture 200 has through holes 226 extending from the base of its concavities 222. A one-way valve 272 in the nature of a mitre valve is provided within each through hole. Each one-way valve allows fluid (air and saliva) to pass from the upper surface 220 of the denture to the lower surface 230.

Denture 200 functions similarly to denture 10 of FIG. 1A with the one-way valves 272 allowing air to be expelled from the concavities, but not allowing it to return in order to create suction forces which hold the denture in place. Denture 200 is not ideal, however, as it may be more difficult to remove than denture 10.

Figure 9:
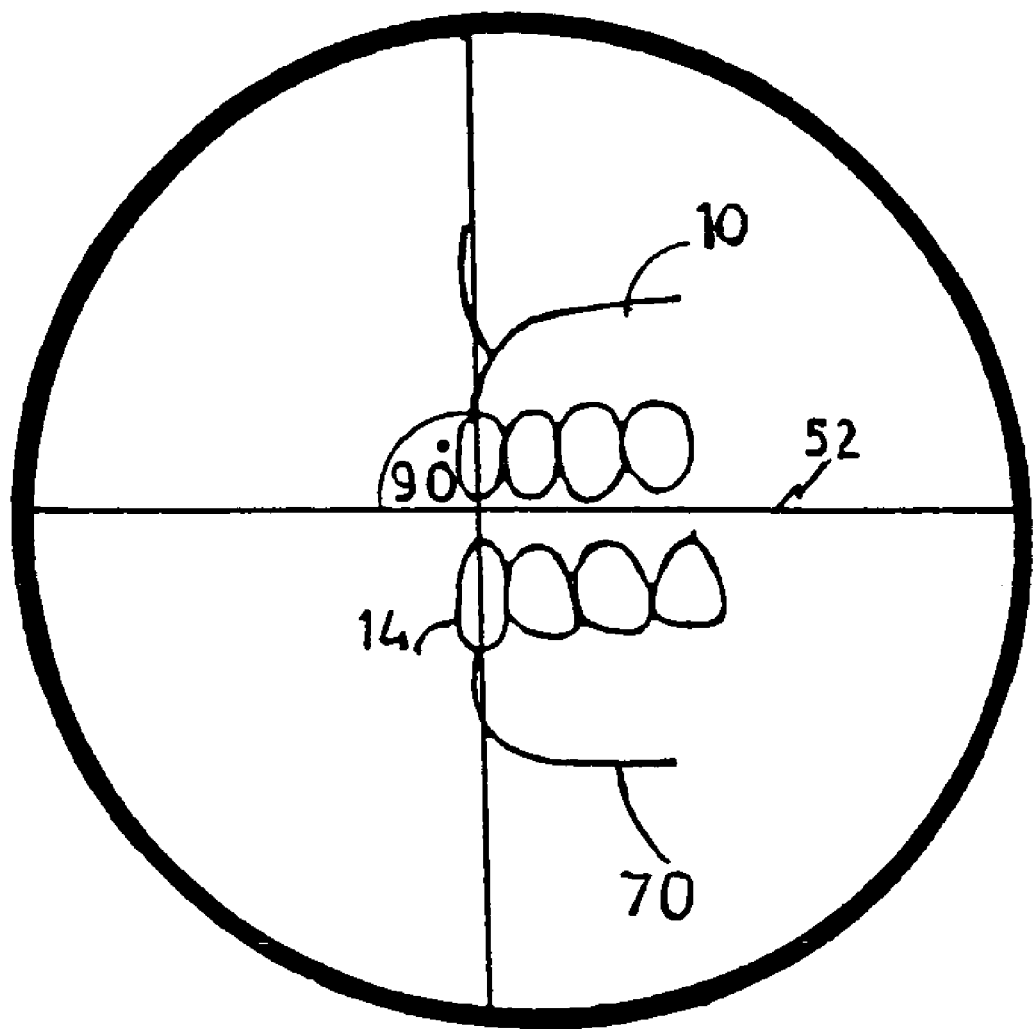
FIG. 9 is a simplified side view of a maxillary and mandibular denture made in accordance with this invention.

With reference to FIG. 9, for proper operation, the maxillary denture 10, and a corresponding mandibular denture 70 constructed in like manner to maxillary denture 10, should have teeth arranged to create a horizontal bite plane 52. This will help maximize the component of the biting force which acts to push tissue into the concavities of the dentures.

To remove denture 10, 100, or 200 from the mouth, a user may hook their thumb around the back edge of the denture and in between the denture and soft tissue 50. The user may then gently peel the denture away from the soft tissue 50. In this connection, denture 10 is the easiest denture to remove due to through holes 26 allowing air to flow between the top surface 20 of the denture and the soft tissue during denture removal. Denture 100 is next easiest to remove since air can be drawn through the membrane 140 which covers holes 26 to between the top surface of the denture and the soft tissue. Denture 200 presents the greatest difficulty in removal because the mitre valves will not allow air to flow to between the top surface of the denture and the soft tissue.

With reference to FIGS. 10A and 10B, removal of the dentures of this invention from the mouth may be facilitated with tool 300. One end of the tool 300 has a tip 302 which may make a 65° angle with the body 304 of the tool. The other end of the tool has a tip 306 which may make a 45° angle with the body 304 of the tool. Tip 306 may also be narrower than tip 302. In use, tip 302 may be slid between the top surface of a maxillary denture at its back edge and the soft tissue of the mouth and used to progressively peel the denture from the mouth. Similarly, tip 306 may be slid between the inside surface of a mandibular denture at its back edge and the soft tissue of the mouth and used to progressively peel the denture from the mouth.

While the maxillary denture illustrated is a full denture, it will be apparent that this invention is equally applicable to partial dentures (i.e., dentures to provide some, but not all of the maxillary or mandibular teeth).

Other modifications will be apparent to those skilled in the art and, therefore, the invention is defined in the claims.

What is claimed is:

1. A denture comprising:
   a body having a plurality of concavities in a first surface of said body, said first surface, in use, abutting soft tissue of a mouth and a plurality of through holes extending from said first surface to an opposite, second, surface, said through holes being spaced from said concavities;
   a porous membrane interposed between said concavities and said through holes.

2. The denture of claim 1 wherein said membrane is microporous.

3. The denture of claim 1 wherein said membrane is provided on said first surface.

4. The denture of claim 3 wherein said membrane is bonded to said first surface of said body.

5. The denture of claim 3 wherein said membrane caps said through holes.

6. The denture of claim 3 wherein said membrane has openings registered with said concavities such that said concavities are free of said material.

7. The denture of claim 6 wherein said membrane has openings registered with said though holes.

8. The denture of claim 1 wherein said denture is a maxillary denture and said first surface is a top surface of said denture.

9. The denture of claim 1 wherein said denture is a mandibular denture and said first surface is a bottom surface of said denture.

10. The denture of claim 1 wherein said concavities are shaped as part spherical cavities.

11. The denture of claim 10 wherein at least some of said concavities are at least three millimeters in diameter at their mouth and have a depth of at least three millimeters.

* * * * *